United States Patent [19]
Creuzet et al.

[11] 4,333,938
[45] Jun. 8, 1982

[54] IMINO DERIVATIVES OF 5-AMINOBENZODIOXOLE-1,3 WHICH ARE USEFUL AS MEDICAMENTS

[75] Inventors: Marie-Helene Creuzet, Bordeaux; Claude Feniou, Pessac; Gisele Prat, Talence; Henri Pontagnier, Pessac, all of France

[73] Assignee: Laboratoires Sarget, Merignac, France

[21] Appl. No.: 162,814

[22] Filed: Jun. 25, 1980

[30] Foreign Application Priority Data

Jul. 16, 1979 [FR] France ................................ 79 18357

[51] Int. Cl.³ .................... C07D 405/12; C07D 407/12
[52] U.S. Cl. ..................................... 424/263; 424/275; 424/282; 542/406; 542/420; 542/422
[58] Field of Search ...................... 542/406, 420, 422; 424/263, 275, 282

[56] References Cited

U.S. PATENT DOCUMENTS 2,876,220  3/1959  Robertson ........................... 544/422
4,144,341  3/1979  Clark et al. .......................... 424/256

FOREIGN PATENT DOCUMENTS 2630764  1/1977  Fed. Rep. of Germany .

OTHER PUBLICATIONS

Wagner et al., Synthetic Organic Chemistry; John Wiley & Sons, New York, N.Y., 1953, pp. 728–729.

Primary Examiner—Arthur P. Demers
Attorney, Agent, or Firm—Oblon, Fisher, Spivak, McClelland & Maier

[57] ABSTRACT

New compounds of the general formula:

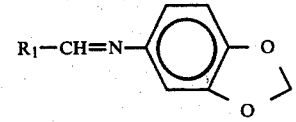

wherein $R_1$ is an unsaturated heterocyclic radical selected from the group consisting of:

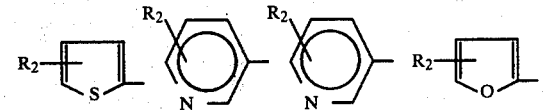

wherein $R_2$ is H or one substituent selected from the group consisting of $CH_3$, halogen, and nitro, are useful as anti-inflammatories and in the oral treatment of diabetes.

12 Claims, No Drawings

IMINO DERIVATIVES OF 5-AMINOBENZODIOXOLE-1,3 WHICH ARE USEFUL AS MEDICAMENTS

BACKGROUND OF THE INVENTION

1. Field of the Invention

This invention relates to new imino derivatives of 5-aminobenzodioxole-1,3 which are useful as medicaments.

2. Description of the Prior Art

Some derivatives of 5-aminobenzodioxole-1,3 are already known. In particular, French Pat. No. 75 21,504, filed July 9, 1975, Publication No. 2,316,938, relates to N-substituted-3-amino-3H isobenzofuranones which contain the 5-aminobenzodioxole-1,3 group.

SUMMARY OF THE INVENTION

We now disclose some new derivatives having the general formula

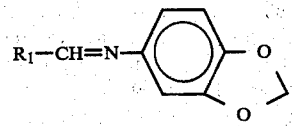

wherein $R_1$ = an unsaturated heterocyclic radical such as

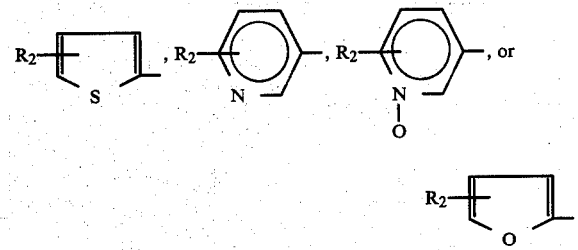

and $R_2$ = H or one or more substituents such as $CH_3$, halogen, or nitro.

DETAILED DESCRIPTION OF THE INVENTION AND PREFERRED EMBODIMENTS

These compounds are useful in therapy by reason of their analgesic and anti-inflammatory activities and have the advantage of being practically devoid of ulcerogenic activity, in contrast to the classical anti-inflammatories.

The compounds of the invention are also useful in the oral treatment of diabetes. Such treatments employ medicaments belonging to two chemical classes, the sulfamides and biguanides. The hypoglycemic sulfamides act via the pancreas by stimulating the cells of the islands of Langerhans. The biguanides act through an extrapancreatic mechanism by increasing the utilization of glucose, by inhibiting the hepatic gluconeogenesis, and by decreasing the digestive absorption of glucose. Nevertheless, they have the drawback of being accompanied by rare, but often fatal, lactic acidosis. This has led to the abandonment of the commercial availability of phenformin in France, only metformin still being available.

The compounds of the present invention are prepared generally by the reaction between 5-aminobenzodioxole-1,3 and an aldehyde $R_1CHO$ wherein $R_1$ has the significance indicated above, in a suitable solvent such as benzene. The water produced in the course of the reaction is eliminated as it is formed.

The practice of the invention will be explained more precisely in the following examples.

EXAMPLE 1

Synthesis of N-thienylidene-5-aminobenzodioxole-1,3

A mixture of 10 g of 5-aminobenzodioxole-1,3, 11 g of 2-thiophencarboxaldehyde and 70 cm³ of benzene is heated to 120° C. with agitation. The water formed in the course of the reaction is eliminated using a Dean-Stark trap. The benzene is driven off by evaporation and the imine is distilled.

Properties:
Molecular weight: 231    Empirical formula: $C_{12}H_9NO_2S$    Yellow solid; insoluble in water
M.P. = 62° C.

| NMR spectrum in CDCL₃, TMS internal standard: | | | |
|---|---|---|---|
| 5.9 ppm | singlet | 2 protons | O—CH₂—O |
| 6.6–7.5 ppm | broad complex | 6 protons | 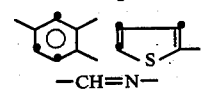 |
| 8.5 ppm | singlet | 1 proton | —CH=N— |

EXAMPLE 2

Synthesis of N-(5-methyl-2-thienylidene)-5-aminobenzodioxole-1,3

A mixture of 10 g of 5-aminobenzodioxole-1,3, 12 g of 5-methylthiophenecarboxaldehyde, and 70 cm³ of benzene is heated at 120° C. with agitation. The water formed in the course of the reaction is eliminated using a Dean-Stark trap. The benzene is removed by evaporation and the imine is purified by distillation. Yield 90%.

Properties:
Molecular weight: 245    Empirical formula: $C_{13}H_{11}NO_2S$
Yellow powder, insoluble in water
M.P. = 73° C.

| NMR spectrum in CDCl₃, TMS internal standard: | | | |
|---|---|---|---|
| 2.5 ppm | singlet | 3 protons | CH₃ |
| 5.8 ppm | singlet | 2 protons | —O—CH₂—O— |
| 6.5–7.2 ppm | broad complex | 5 protons | 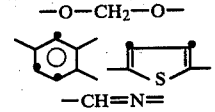 |
| 8.3 ppm | singlet | 1 proton | —CH=N= |

EXAMPLE 3

Synthesis of N-(3-pyridylidene)-5-aminobenzodioxole-1,3

This compound is synthesized by the same procedure as the two previous compounds, starting from a mixture of 10 g of 5-aminobenzodioxole-1,3, 10 g of pyridine-3-carboxaldehyde, and 70 cm³ of benzene.

Properties:
Molecular weight: 226.2    Empirical formula: $C_{13}H_{10}N_2O_2$
Yellow solid, insoluble in water
M.P. = 91° C.

NMR spectrum in CDCl₃, TMS internal standard:

-continued

| 5.9 ppm | singlet | 2 protons | O—CH$_2$—O |
| 6.7-9 ppm | broad complex | 8 protons | |

—CH=N— (singlet at 8.4 ppm)

EXAMPLE 4

Synthesis of N-(3-methyl-2-thienylidene)-5-aminobenzodioxole-1,3

This imine is synthesized as described in Example 2. After distillation it is dissolved in ethyl ether and petroleum ether is added thereto to induce crystallization. It is subsequently filtered and dried under vacuum at 50° C. Yield 85%.

Properties:

Molecular weight: 245  Empirical formula: $C_{13}H_{11}NO_2S$
Yellow powder, insoluble in water
M.P. = 69° C.

NMR spectrum in CDCl$_3$, TMS internal standard:

| 2.4 ppm | singlet | 3 protons | CH$_3$ |
| 5.9 ppm | singlet | 2 protons | —O—CH$_2$—O |
| 6.6-7.4 ppm | broad complex | 5 protons | |
| 8.5 ppm | singlet | 1 proton | —CH=N— |

Pharmacological results:

The percentages of mortality produced by the compounds of this invention when administered orally to Swiss mice are shown in Table 1. The animals, free from specific pathogenic organisms were housed in an air conditioned room for 24 to 48 hours before the start of the experiment. They were separated into groups of 5 males and 5 females. The materials were administered to animals which had been fasted for 24 hours by means of a gastric tube in suspension in a 6% thickened julep using a volume equivalent to 0.1 ml per 10 g of body weight. After administration, the animals were observed for one hour, and then at one hour intervals during the first day. They remained under observation for two weeks before being sacrificed and autopsied.

TABLE 1

| | TOXICITY IN THE MOUSE | | | | | | | |
|---|---|---|---|---|---|---|---|---|
| Compound of | % mortality as a function of the dose expressed in mg/kg | | | | | | | |
| Example | 500 | 750 | 1000 | 1250 | 1500 | 1750 | 2000 | 3000 |
| 1 | | | 0 | | 20 | | 60 | 70 |

TABLE 1-continued

| | TOXICITY IN THE MOUSE | | | | | | | |
|---|---|---|---|---|---|---|---|---|
| Compound of | % mortality as a function of the dose expressed in mg/kg | | | | | | | |
| Example | 500 | 750 | 1000 | 1250 | 1500 | 1750 | 2000 | 3000 |
| 2 | | 10 | 20 | 0 | 60 | | | |
| 3 | 0 | | 10 | | | | 100 | |
| 4 | | 10 | 10 | | 60 | 20 | 20 | |

The toxicities of the compounds of Examples 2 and 3 were determined in the Wistar rat. The protocol which was followed was the same as that described for the mice, except that the compounds were administered in a volume equivalent to 0.5 ml per 100 g of body weight of rat. The product of Example 2 showed no mortality at 3000 mg/kg. The product of Example 3 produced no mortality at 2000 mg/kg and 20% mortality at 3000 mg/kg.

The analgesic activity was determined in the male Swiss mouse using phenylbenzoquinone (PBQ) as the challenging agent (variation of the method of Siegmund et al, Proc. Soc. Exp. Biol. Med. 1975, 95, 729-31). Twenty five minutes after oral administration of the compounds to be tested in suspension in a 6% thickened julep, a solution of PBQ was injected, and the mice were observed at the end of five minutes and during the following 5 minutes. The results are shown in Table 2. The ED$_{50}$ was determined by the method of Lichfield and Wilcoxon.

TABLE 2

| Compound of | % analgesic activity as a function of the dose expressed in mg/kg | | | | | | | | |
|---|---|---|---|---|---|---|---|---|---|
| Example | 50 | 75 | 100 | 125 | 150 | 200 | 250 | 300 | ED$_{50}$ |
| 1 | | | 34 | 43 | 69 | 73 | | | 130 (99-171) |
| 2 | | 23 | 19 | | | 49 | 51 | 40 | |
| 3 | 23 | | 44 | | | 65 | | 92 | 110 (67-179) |
| 4 | | 21 | 40 | | 37 | 62 | | 67 | 170 (107-270) |

Table 3 gives the percentage of inhibitory activity with respect to carageenan-induced edema. The inflammation is produced in the male Wistar rat by injection of 0.1 ml of a 0.5% suspension of carageenan in physiological serum, into the muscular fascia of the metatarsal region of the hind foot of the animal. The test substance is administered orally at the same time as the carageenan or 30 or 60 min before carageenan. The edema is measured by plethysmometry three hours after the adminstration of the carrageenan.

TABLE 3

| Treatment | Time of Administration of the Compound | % inhibiting activity on carrageenen - induced edema as a function of the dose expressed in mg/kg | | | | | | | | | |
|---|---|---|---|---|---|---|---|---|---|---|---|
| | | 25 | 50 | 75 | 100 | 125 | 150 | 200 | 225 | 300 | 400 | 450 |
| Compound of Example 1 | T$_o$ | 19 | 41 | | 52 | | | 56 | | | 58 | |
| Compound of Example 2 | T$_o$ | | | | 30 | | 64 | 33 | | 59 | | |
| | T$_o$ − 30 | | | 21 | | | 47 | | | 61 | | |
| | T$_o$ − 60 | | | 15 | | | 26 | | 49 | 66 | | |
| Compound of Example 3 | T$_o$ | | | | 57 | | | 28 | | | 55 | |
| | | | | | 29 | | | 36 | | | 39 | |
| | T$_o$ − 30 | 34 | 41 | 44 | 50 | | 53 | 66 | | | 67 | |
| | | | 38 | | 41 | | | | | | 72 | |
| | T$_o$ − 60 | 25 | 42 | 40 | 39 | | | 58 | | | 69 | |

TABLE 3-continued

| Treatment | Time of Administration of the Compound | % inhibiting activity on carrageenen - induced edema as a function of the dose expressed in mg/kg | | | | | | | | | |
|---|---|---|---|---|---|---|---|---|---|---|---|
| | | 25 | 50 | 75 | 100 | 125 | 150 | 200 | 225 | 300 | 400 | 450 |
| Compound of Example 4 | $T_o$ | | | 35 | | | 35 | | | 68 | | |
| Aspirin | $T_o$ | | | 40 | | | 46 | | | 68 | | 64 |
| Niflumic Acid | $T_o$ | | | 37 | 27 | 40 | 37 59 | | | | | |

Table 4 shows the percentage of inhibitory activity with respect to edema produced by serotonin. In the Wistar rat inflammation is induced by intrapedal injection of 0.1 ml of a 0.02% solution of serotonin in physiological serum. The test substance is administered orally 30 minutes before the serotonin and the edema is measured by plethysmometry one hour after its release.

TABLE 4

| Compound of Example | % Inhibitory activity as a function of the dose expressed in mg/kg | | |
|---|---|---|---|
| | 100 | 200 | 400 |
| 2 | 39 | 29 | 37 |
| 3 | 27 | 21 | 26 |

Table 5 shows the activity with respect to carrageenan-induced granulomas. Male Wistar rats weighing 130 to 150 grams were given a subcutaneous injection in the central part of the skin of the back of 0.5 ml of an aqueous suspension of carrageenan. Two doses of the test substance are administered, one 30 minutes before and the other 6 hours after carrageenan. At the end of 24 hours the rats were sacrificed and the granulomas were removed and weighed before and after drying for 24 hours at 50° C. The difference in weight of the granulomas wet and dry represents the exudate

TABLE 5

| Compound of Example | Dose in mg/kg administered twice | Weight of wet granuloma | | Weight of dry granuloma | | Exudate | |
|---|---|---|---|---|---|---|---|
| | | % activity | % animals 30% protected | % activity | % animals 30% protected | % activity | % animals 30% protected |
| 1 | 200 | 6 | 12.5 | 1 | 12.5 | 6 | 12.5 |
| 2 | 100 | 32 | 62 | 34 | 62 | 31 | 62 |
| | | 15 | 25 | 14 | 25 | | |
| | 150 | 5 | 25 | 1 | 25 | 6 | 25 |
| | | 22 | 14 | 24 | 14 | 22 | 14 |
| | 200 | 39 | 75 | 41 | 75 | 39 | 75 |
| | | 24 | 50 | 22 | 50 | | |
| | 300 | 18 | 25 | 9 | 25 | 18 | 2 |
| 3 | 100 | 15 | 25 | 12 | 12 | 15 | 25 |
| | | 25 | 37 | 22 | 25 | 25 | 37 |
| | 200 | 27 | 37 | 27 | 37 | 27 | 37 |
| | | 33 | 75 | 32 | 75 | 34 | 75 |
| | | 34 | 71 | 33 | 71 | 38 | 71 |
| | 250 | 36 | 75 | 33 | 62 | 36 | 75 |
| | 300 | 35 | 87 | 37 | 62 | 35 | 87 |
| | | 43 | 75 | 41 | 75 | 43 | 75 |
| 4 | 100 | 20.5 | 38 | 16 | 31 | 21 | 38 |
| | 200 | 34 | 71 | 31 | 64 | 34.5 | 71 |
| | 300 | 44.5 | 75 | 42.5 | 67 | 44.5 | 75 |
| Niflumic Acid | 25 | 42.5 | 100 | 41.5 | 87 | 42.5 | 100 |

These results allowed calculation of the AD$_{50}$ (doses which protect 50% of the animals to the extent of 30% with respect to the wet weight of the granuloma) for the compounds of Examples 2 and 3. These AD$_{50}$ are respectively 175(142–215) and 175(150–205) mg/kg.

Table 6 shows the activities with respect to cotton pellet granulomas. Two cotton pellets weighing 70 mg were implanted under the back skin of male Sprague-Dawley rats anesthetized with ether. Starting the next day, the compound was administered orally daily for 10 days. The rats were sacrificed and the pellets were removed and weighed before and after drying at 50° C. for 24 hours. The weights used were those obtained after deduction of the weight of the implants. The average of the quantities so calculated was determined for each group and compared to the averages of the control group.

TABLE 6

| Compound of Example | Dose | % inhibition with respect to | |
|---|---|---|---|
| | | wet pellets | dry pellets |
| 2 | 150 | 12 | 5 |
| | 300 | 17 | 23 |
| 3 | 150 | 0 | 5 |
| 4 | 150 | 13 | 10 |
| | 300 | 14 | 19 |
| Niflumic Acid | 50 | 3 | 12 |

The ulcerogenic activity was determined in the female Wistar rat using a variation of the procedure described by J. M. Lwoff, J. Pharmacol. 1971, 3, 1, 81-3. The test substance was administered daily for 3 days to the animals maintained on a aqueous diet. The stomachs were removed after 1, 2, and 3 days of treatment and the ulcerations were classified from 0 to 4. The ulceration index is calculated for each group of animals as the product (average of the classes x the percentage of animals afflicted), while distinguishing acute ulcerations from ulcers which were in the process of healing. The results are presented in Table 7.

TABLE 7

| Treatment | Dose administered in mg/kg | Ulceration Index | | | | | |
|---|---|---|---|---|---|---|---|
| | | acute | | | healing | | |
| | | Day 1 | Day 2 | Day 3 | Day 1 | Day 2 | Day 3 |
| Control | | 0 | 1 | 36 | 0 | 0 | 2 |
| Compound of Example 2 | 150 | 6 | 2 | 48 | 0 | 6 | 28 |
| Compound of Example 3 | 150 | 6 | 20 | 33 | 0 | 6 | 12 |
| Compound of Example 4 | 150 | 0 | 0 | 72 | 0 | 8 | 16 |
| Niflumic Acid | 100 | 330 | 1 | 119 | 0 | 400 | 378 |

The antidiabetic activity of the compounds of this invention was demonstrated in the following manner.

Female rats weighing 180–200 grams were given an intraperitoneal dose on day J0 of 100 mg/kg of streptozotocin in a 0.05 M citrate buffer at a pH of 4.5 calculated as 0.5 ml per 100 g of body weight. On day J2 hyperglycemic animals were selected by determining the blood sugar level by the orthotoludine method in a stream continuously removed from the retroorbital sinus. Only those animals were retained which had a blood sugar level equal to or greater than 2.5 g/l. On day J3, without previous fasting, the selected animals received the treatment. This consisted of oral administration of the test compound in a 6% aqueous suspension of gum arabic at a volume of 0.5 ml per 100 g of body weight.

The animals were sacrificed one, two, or four hours after the treatment and their blood sugar levels were determined. Each group of animals was compared to a control group of animals which received only the suspension of gum arabic. Metformin was the substance chosen as the control.

The results are given in Table 8 which indicates the percentage of decrease in the blood sugar level produced by the treatment. The symbol NS indicates that the difference between the blood sugar level in the treated animals and the control animals is not significant; the symbol S signifies that the difference is significant by Student's test at $p \leq 0.05$.

TABLE 8

| PRODUCT | Percentage Decrease in the Blood Sugar as a Function of the Dose Administered Expressed in mg/kg | | | | | | | |
|---|---|---|---|---|---|---|---|---|
| | 50 | | 100 | | 200 | | 400 | |
| N-(5-methyl-2-thienylidene)-5-aminobenzodioxole-1,3 | | | | | | | | |
| Treatment 1 h before sacrificing | 13 | S | 22 | S | 24 | S | | |
| 2 h before sacrificing | 22 | S | 32 | S | 35 | S | | |
| 4 h before sacrificing | 12 | S | 27 | S | 31 | S | | |
| N-(3-pyridylidene)-5-aminobenzodioxole-1,3 | | | | | | | | |
| Treatment 1 h before sacrificing | 16 | S | | NS | | NS | | |
| 2 h before sacrificing | | NS | 27 | S | 19 | S | | |
| 4 h before sacrificing | 23 | S | 29 | S | 28 | S | | |
| Metformin | | | | | | | | |
| Treatment 1 h before sacrificing | | | | | | NS | 14 | S |
| 2 h before sacrificing | | | | | | NS | | NS |
| 4 h before sacrificing | | | | | | NS | 15 | S |

By reason of their pharmacological properties, the compounds of this invention are useful in medicine for treating diseases involving pain and inflammation. For example, the compounds can be prescribed in treatment of rheumatic diseases (for example, inflammatory and degenerative rheumatism, affliction of the joints and other parts, and in acute crises of gout), in treatment of trauma (for example, sprains, fractures, dislocations, and tendonitis), in surgery (pre- and post-operative pain, physical therapy), in treatment of dermatophlebitis (phlebitis, periphlebitis, cutaneous ulcers) as well as in painful and inflammatory pathologies in the treatment of dental problems, cancer, visceral diseases, vascular diseases, neurological diseases and the like.

The compounds are also useful in therapy, in combination with diet, in the treatment of diabetes of the non-insulin-dependent type. They can be employed in certain types of insulin-dependent diabetes, in combination with hypoglycemic sulfamides or insulin therapy.

The compounds can be administered, in combination with the usual excipients, orally, rectally, percutaneously, or in numerous galenic preparations, such as compresses, suppositories, pomades, gels and the like.

The oral forms contain 100 to 500 mg of active ingredient in a unitary dose, the rectal forms contain 100 mg to 1 gram and the topical forms contain 2 to 10%. The average daily dose is from 200 mg to 2 g of active ingredient orally or rectally.

What is claimed as new and desired to be secured by Letters Patent of the United States is:

1. A compound of the general formula

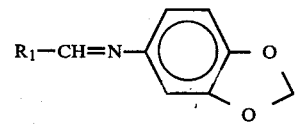

wherein $R_1$ is an unsaturated heterocyclic radical selected from the group consisting of

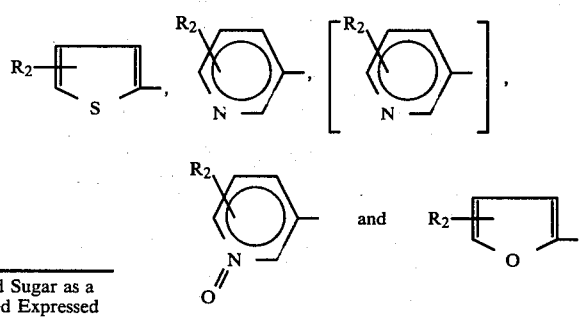

wherein R₂ is H or one substituent selected from the group consisting of CH₃, halogen, and nitro.

2. The compound of claim 1, having the formula

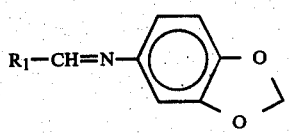

wherein R₁ is selected from the group consisting of

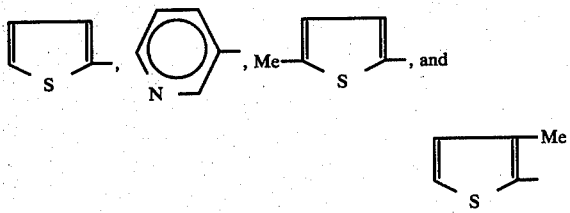

3. A pharmaceutical composition comprising an amount of a compound of claim 1 or claim 2 effective in treating inflammation and a pharmaceutically acceptable non-toxic excipient.

4. A pharmaceutical composition comprising an amount of a compound of claim 1 or claim 2 effective in treating non-insulin-dependent diabetes and a pharmaceutically acceptable non-toxic excipient.

5. An analgesic pharmaceutical composition for oral administration comprising 100 to 500 milligrams of a compound of claim 1 or claim 2 and a pharmaceutically acceptable non-toxic excipient.

6. An analgesic pharmaceutical composition for rectal administration comprising 100 milligrams to 1 gram of a compound of claim 1 or claim 2 and a pharmaceutically acceptable non-toxic excipient.

7. An analgesic pharmaceutical composition for topical administration comprising 2 to 10% by weight of a compound of claim 1 or claim 2 and a pharmaceutically acceptable non-toxic excipient.

8. An anti-inflammatory pharmaceutical composition for oral administration comprising 100 to 500 milligrams of a compound of claim 1 or claim 2 and a pharmaceutically acceptable non-toxic excipient.

9. An anti-inflammatory pharmaceutical composition for rectal administration comprising 100 milligrams to 1 gram of a compound of claim 1 or claim 2 and a pharmaceutically acceptable non-toxic excipient.

10. An anti-inflammatory pharmaceutical composition for topical administration comprising 2 to 10% by weight of a compound of claim 1 or claim 2 and a pharmaceutically acceptable non-toxic excipient.

11. An anti-diabetic pharmaceutical composition for oral administration comprising 100 to 500 milligrams of a compound of claim 1 or claim 2 and a pharmaceutically acceipient.

12. An anti-diabetic pharmaceutical composition for rectal administration comprising 100 milligrams to 1 gram of a compound of claim 1 or claim 2 and a pharmaceutically acceptable non-toxic excipient.

* * * * *